United States Patent [19]

Dugger

[11] Patent Number: 5,420,283
[45] Date of Patent: May 30, 1995

[54] RESOLUTION OF (R)-2-BENZYLSUCCINIC ACID 4-[4-(N-T-BUTOXYCARBONYLME-THYLAMINO)-PIPERIDINE] AMIDE

[75] Inventor: Robert W. Dugger, Mystic, Conn.

[73] Assignee: Pfizer Inc., New York, N.Y.

[21] Appl. No.: 101,146

[22] Filed: Aug. 2, 1993

[51] Int. Cl.$^6$ .................. C07D 211/06; C07D 211/56
[52] U.S. Cl. ...................... 546/223; 546/226
[58] Field of Search ................ 546/223, 226

[56] References Cited

U.S. PATENT DOCUMENTS 4,533,481 8/1985 Jahnke ...................... 252/49.6

FOREIGN PATENT DOCUMENTS 417698 3/1991 European Pat. Off. .
0438233 7/1991 European Pat. Off. .

OTHER PUBLICATIONS

Yamaguchi et al "Asymmetric Induction Polymerization of Monomer Salts" Makromol. Chem. 191 1243–51 (1990).
Parker et al "Direct NMR Assay of Enantiomeric Compositions of Amines and β-Amino Alcohols" Tetrahedron 43 5451–56 (1987).
Jacob J. Plattner et. al., entitled *Renin Inhibitors, Dipeptide Analogues of Angiotensinogen Utilizing a Structurally Modified Phenylalanine Residue To Impart Proteolytic Stability*, J. Med. Chem. 1988, 31, 2277–2288.
Jacques, Collet and Wilen, *Enantiomers, Racemates and Resolutions*, pp. 253–254 (John Wiley & Sons, Inc. 1981).
Morrison, *Asymmetric Synthesis*, vol. 1, p. 3, (Academic Press, 1983).
Paul Newman, *Optical Resolution Procedures for Chemical Compounds*, vol. 2, Part 1, p. 2, (Optical Resolution Information Center, Manhattan College, published 1981).
H. Harada et al., A Practical Synthesis of the [(2R)-3-(-Morpholinocarbonyl)-2(1-naphthylmethyl)propionyl-]-L-histidine Moiety ($P_4$–$P_2$) in Renin Inhibitors, 55, J. Org. Chem., 1679–1682 (1990).
T. Nishi et al., Asymmetric Synthesis of 2-Substituted-3-aminocarbonyl Propionic Acid, 37(8), Chem. Pharm. Bull., 2200–2203 (1989).
Y. Ito et al., An Efficient Synthesis of Methyl N-[2-(R-)-(1-Naphthylmethyl)-3-(Morpholinocarbonyl)Propionyl]-(S)-Histidinate, The Key Synthetic Intermediate of Renin Inhibitors, 31(19), Tetrahedron Letters, 2731–2734 (1990).
J. Plattner et al., Renin Inhibitors, Dipeptide Analogues of Angiotensinogen Utilizing a Structurally Modified Phenylalanine Residue To Impart Proteolytic Stability, 31, J. Med. Chem., 2277–2288 (1988).

*Primary Examiner*—Celia Chang
*Attorney, Agent, or Firm*—Peter C. Richardson; Paul H. Ginsburg; Garth Butterfield

[57] ABSTRACT

This invention relates to with a novel synthesis of (R)-2-benzylsuccinic acid 4-[4-(N-t-butoxycarbonyl-methylamino)-piperidine]amide from racemic intermediates. The racemic (R)-2-benzylsuccinic acid 4-[4-(N-t-butoxycarbonyl-methylamino)piperidine]amine is resolved through the formation of diasteromic salts with (S)-cyclohexylethylamine or (R)-cyclohexylethylamine. The pure diasteromic salt can be subsequently hydrolyzed with dilute acid to yield the pure enantiomer of (R)-2-benzylsuccinic acid 4-[4-(N-t-butoxycarbonyl-methylamino) piperidine]amide.

12 Claims, No Drawings

RESOLUTION OF (R)-2-BENZYLSUCCINIC ACID 4-[4-(N-T-BUTOXYCARBONYLMETHYLAMINO)-PIPERIDINE] AMIDE

BACKGROUND OF THE INVENTION

This invention relates to a process for resolving (R)-2-benzylsuccinic acid 4-[4-(N-t-butoxycarbonyl-methylamino)-piperidine]amide. (R)-2-benzylsuccinicacid4-[4-(N-t-butoxycarbonyl-methylamino)-piperidine] amide is an intermediate in the synthesis of theorally active renin inhibitor 4-[4-(N-methylamino)piperidine ]-(R)-2-benzylsuccinamide-(SMe)cystein-nor-cyclostatine hydrochloride, which is an an antihypertensive agent.

Renin is a proteolytic enzyme which is known to be active in vivo in cleaving the naturally occuring plasma glycoprotein angiotensinogen. In the case of human angiotensinogen, renin cleaves the bond between the leucine (10th) and valine (11th) amino acid residues at the N-terminal end of the angiotensinogen. The circulating N-terminal decapeptide known as angiotensin I that is formed by the cleaving action of renin is subsequently broken down by the body to an octapeptide known as angiotensin II. Angiotensin II is known to be a potent pressor substance, i.e., a substance that is capable of inducing a significant increase in blood pressure and is believed to act by causing the constriction of blood vessels and the release of the sodium retaining hormone aldosterone from the adrenal gland. The renin-angiotensinogen system has been implicated as a causative factor in certain forms of hypertension and congestive heart failure. The renin inhibitors that can be made from the compounds of the invention alleviate the adverse effects of the functioning renin-angiotensinogen system by inhibiting the angiotensinogen cleaving action of renin.

The renin inhibitors that can be prepared from the intermediates of this invention are described in U.S. patent application Ser. No. 08/028,038, which was filed on Mar. 8, 1993. U.S. patent application Ser. No. 08/028,038 also describes the pharmacology of 4-[4-(N-methylamino)piperidine]-(R)-2-benzylsuccinamide-(SMe)cysteine-norcyclostatine hydrochloride.

SUMMARY OF THE INVENTION

The present invention relates to a process for resolving racemic or optically enriched 2-benzylsuccinic acid 4-[4-(N-t-butoxycarbonyl-methylamino)-piperidine]amide, comprising reacting racemic 2-benzylsuccinic acid 4-[4-(N-t-butoxycarbonylmethylamino)-piperidine] amide or an optically active mixture of (R)-2-benzylsuccinic acid 4-[4-(N-t-butoxycarbonyl-methylamino)-piperidine]amide and (S)-2-benzylsuccinic acid 4-[4-(N-t-butoxycarbonyl-methylamino)-piperidine]amide with a resolving agent that is ethyl -(+)-1-cyclohexyethylamine.

The present invention also relates to a process for preparing a compound of the formula

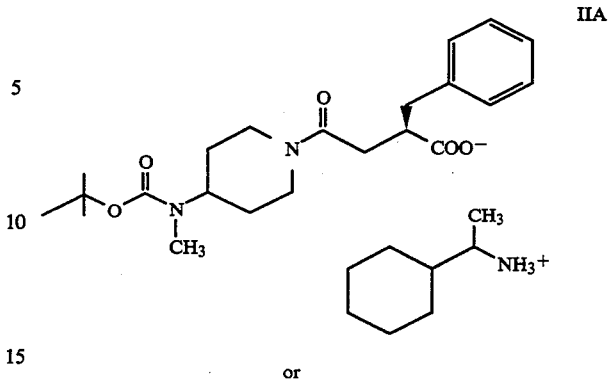

comprising reacting (S)-(+)-1-cyclohexylethylamine with either racemic 2-benzylsuccinic acid 4-[4-(N-t-butoxycarbonyl-methylamino)-piperidine]amide or an optically active mixture of (R)-2-benzylsuccinic acid 4-[4-(N-t-butoxycarbonyl-methylamino)-piperidine]amide and (S)-2-benzylsuccinic acid 4-[4-(N-t-butoxycarbonyl-methylamino)-piperidine] amide to form a compound of formula IIA, or reacting (R)-(−)-1-cyclohexylethylamine with either racemic 2-benzylsuccinic acid 4[4-(N-t-butoxycarbonyl-methylamino)piperidine] amide or an optically active mixture of (R)-2-benzylsuccinic acid 4-[4-(N-t-butoxycarbonyl-methylamino)-piperidine]amide and (S)-2-benzylsuccinic acid 4-[4-(N-t-butoxycarbonyl-methylamino)-piperidine]amide to form a compound of the formula IIB.

The present invention relates to the above process wherein the compound of formula IIA or IIB formed is neutralized to form, respectively, (R)-2-benzylsuccinic acid 4-[4-(N-t-butoxycarbonyl-methylamino)-piperidine]amide or (S)-2-benzylsuccinic acid 4-[4-(N-t-butoxycarbonyl-methylamino)-piperidine]amide.

The present invention relates to a novel salt of the formula

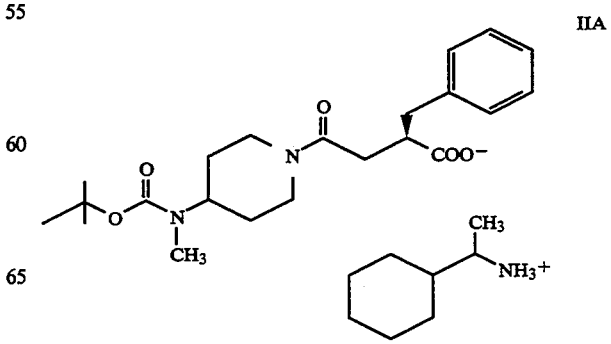

-continued
or
IIB
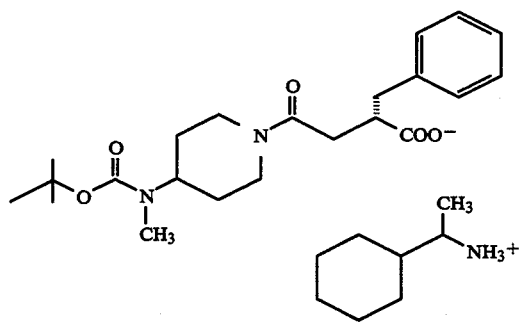
A preferred embodiment of the present invention relates to a salt of the formula
IIA'
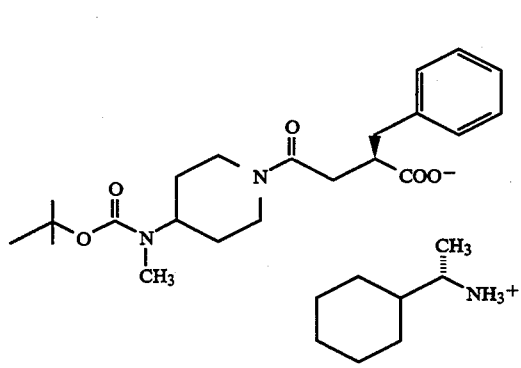
DETAILED DESCRIPTION OF THE INVENTION
Reaction scheme 1 illustrates the preparation of (R)-2-benzylsuccinic acid 4-[4-(N-t-butoxycarbonyl-methylamino) piperidine]amide.
Scheme 1
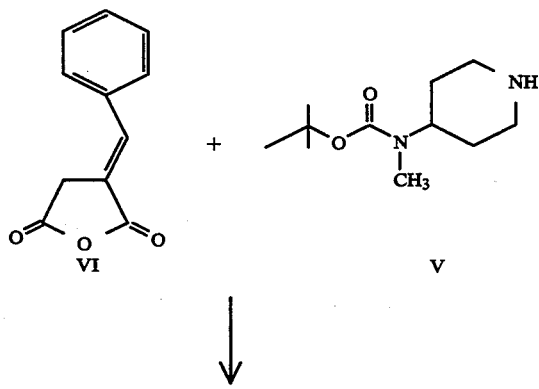

Scheme 2

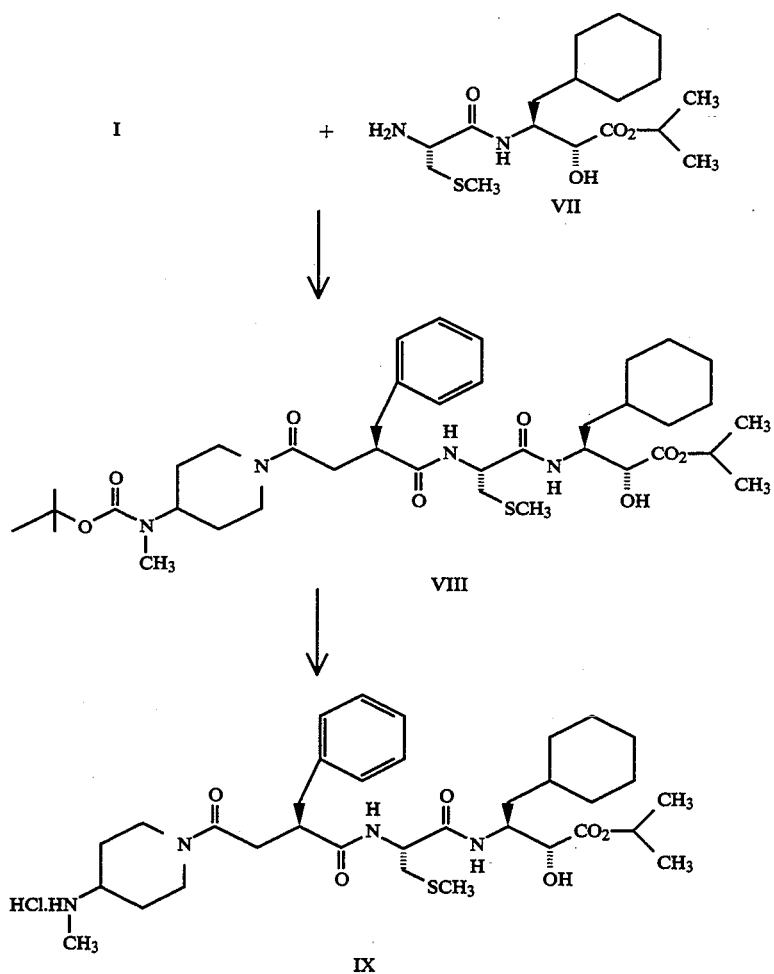

As shown in Scheme 1, the compound of formula VI is reacted with the t-butoxycarbonyl (BOC) protected amine of the formula V or an acid addition salt thereof to form the compound of the formula IV. The coupling of the amine is facilitated by the addition of a base, preferably sodium carbonate. Examples of other bases are triethylamine, pyridine or sodium acetate. When an acid addition salt of the amine is used rather than the amine, it is preferable to add 1–2 equivalents of base. The most common acid addition salts are selected from hydrochloride, hydrobromide, and phosphoric acid. Preferably the free base of the amine is reacted with the compound of formula VI in about an 80:20 isopropaol/water solution at about 20° C. with Na$_2$CO$_3$ as the base.

The foregoing reaction is conducted in a polar solvent, or mixtures of polar solvents. Suitable solvents include acetonitrile, dimethylformamide, dioxane, tetrahydrofuran, dimethoxyethane, water and mxitures thereof. Preferred solvents are mixtures of low molecular weight alcohols such as methanol, ethanol and isopropyl alcohol with water. The temperature of the foregoing reaction is generally about 0° C. to about 50° C., preferably ambient temperature (i.e., about 20–25° C.).

The compound of formula IV so formed is reduced to form a racemic compound of formula III. The reducing agent is hydrogen in combination with a suitable noble metal catalyst such as platinum or palladium. The preferred catalysts are palladium based catalysts such as palladium on carbon and palladium hydroxide on carbon. Hydrogen pressures from 1–1000 p.s.i. may be employed; pressures from 10 to 70 p.s.i. are preferred.

The foregoing reaction is conducted in an inert solvent, preferably a polar solvent. Suitable solvents include methanol, ethanol, isopropyl alcohol dimethylformamide, dioxane, tetrahydrofuran, dimethoxyethane and water. Preferred solvents are low molecular weight alcohols such as methanol, ethanol and isopropyl alcohol. The temperature of the foregoing reaction is generally about 0° C. to about 50° C., preferably ambient temperature (i.e. about 20–25° C.).

The racemic acid of formula III so formed is resolved to yield the (R) or (S) isomer of formula I by formation of an amine salt with, respectively, (S)-(+)-1cyclohexylethylamine or (R)-(−)-1-cyclohexylethylamine in an appropriate solvent. The racemic acid of formula III is resolved by recrystallizing the racemate of formula III with (S)-(+)-1 -cyclohexylethylamine or (R)-(−)-1-cyclohexylethylamine in an organic solvent to yield a diastereoisomerical salt of formula II enriched in, respectively, the (R)- or (S)-isomer of formula I. The salt so formed may be repeatedly recrystallized from the same or different solvent or may be directly converted to the pure enantiomer of formula I.

An appropriate solvent for the foregoing resolution is any solvent capable of dissolving the reactants and selectively dissolving one of the two optically active salts formed (i.e., the compounds of formula IIA and IIB above) while causing the other to precipitate out of solution. Suitable solvents include acetone, acetonitrile, dioxane, ethyl acetate, tetrahydrofuran, dimethoxyethane, methanol, ethanol, 2-propanol and methylethylketone. The preferred solvent is acetone. The temperature of the foregoing resolution is first elevated to between 20° C. and 110° C. to ensure complete solution of the starting materials. The solution is then allowed to cool to about 20–25° C. to afford the diastereoisomeric salt.

When (S)-(+)-1-cyclohexylethylamine is used as the resolving agent, as described above, the (S)-(+)-1-cyclohexylethylamine salt of (R)-2-benzylsuccinic acid 4-[4-(N-t-butoxycarbonyl-methylamino)piperidine]amide precipitates out of solution and can be physically separated by methods well known to those skilled in the art. The S-(+)-1-cyclohexylethylamine salt of the opposite enantiomer (S)-2-benzylsuccinic acid 4-[4-(N-t-butoxycarbonylmethylamino)piperidine]amide remains in solution. When R-(−)-1-cyclohexylethylamine is used as the resolving agent, the R-(−)-1-cyclohexylethylamine salt of (S)-2-benzylsuccinic acid 4-[4-(N-t-butoxycarbonyl-methylamino)piperidine]amide precipitates out of solution, while the R-(−)-1-cyclohexylethylamine salt of (R)-2-benzylsuccinic acid 4-[4-(N-t-butoxycarbonyl-methylamino)piperidine]amide remains in solution.

Neutralization of the cyclohexylethylamine salts of and (R)-2-benzylsuccinic acid 4-[4-(N-t-butoxycarbonyl-methylamino)-piperidine]amide or (S)-2-benzylsuccinic acid 4-[4-(N-t-butoxycarbonyl-methylamino)-piperidine]amide to form the corresponding optically active free acids may be accomplished using methods well known in the art. For example, such neutralization may be accomplished by reacting the cyclohexylethylamine salts with a base such as an alkali or alkaline earth metal hydroxide, carbonate or bicarbonate (e.g., potassium hydroxide, magnesium hydroxide, sodium carbonate or sodium bicarbonate). Suitable solvents for the hydrolysis step include chlorohydrocarbons, ethers, benzene, toluene and water, as well as mixtures of the foregoing solvents (e.g., diethyl ether, diisopropyl ether, methylene chloride, or methylene chloride/water). Suitable temperatures range from about 15° C. to about 100° C., with room temperature being preferred.

The compound of formula I may be converted into the renin inhibitor 4-[4-(N-methylamino)piperidine-(R)-2-benzylsuccinamide-(SMe)cysteine-norcylostatinehydrochloride by the processes described in U.S. patent application Ser. No. 08/028,038, filed Mar. 9, 1993, which is a continuation-in-part of copending U.S. patent application Ser. No. 638,238, filed Jan. 4, 1991 and now abandoned. The European counterpart of the latter application is now available to the public as Published European Patent Application No. EP438233A2, published Jul. 24, 1991. All of the aforesaid patent applications are now herein incorporated by reference in their entirety.

Scheme 2 illustrates one of the processes described in U.S. Pat. Ser. No. 08/028,038, whereby the intermediate of formula I is converted to a known renin inhibitor of formula IX. Peptides of the formula IX can be prepared in two steps beginning with a compound of formula I. The compounds of the formula I are first coupled to a peptide fragment of formula VII, or its hydrochloride salt, to form a peptide of the formula VIII. A peptide coupling reagent is used to facilitate the formation of the peptide bond between the two fragments by activating the carboxylic acid functionality on the fragment of formula I. Examples of suitable coupling reagents are dicyclohexylcarbodiimide/hydroxybenzotriazole (HBT), N-3-dimethylaminopropyl-N'-ethylcarbodiimide/HBT, 2-ethoxy-1-ethoxycarbonyl-1-2-dihydroquinoline (EEDQ), carbonyl diimidazole (CDI)/HBT, and diethylphosphorylcyanide.

The coupling reaction is performed in an inert solvent, preferably an aprotic solvent. Suitable solvents include acetonitrile, dichloromethane, chloroform, ether, tetrahydrofuran (THF) and dimethylformamide. The preferred solvent is dichloromethane. The temperature of the foregoing reaction is generally about −78° C. to about 100° C. Such coupling reactions are preferably conducted at ambient temperature.

The t-butoxycarbonyl (BOC) protected peptide of formula VIII so formed is then deprotected, by conventional deprotection methods familiar to those skilled in the art, to form the amine hydrochloride of formula IX. Hydrogen chloride may be in the form of a saturated solution of hydrogen chloride with an alcohol, acetonitrile, ether or other low boiling organic solvent capable of dissolving hydrogen chloride gas. Preferably the hydrogen chloride is added to ether.

The compounds of the formula I may be used to prepare the renin inhibitor 4-[4-(N-methylamino)piperidine]-(R)-2-benzylsuccinamide-(SMe)cysteine-nor-cyclostatine and the pharmaceutically acceptable salts thereof, exhibit antihypertensive activity in vivo in mammals, including humans. The renin inhibitor 4-[4-(N-methylamino)piperidine]-(R)-2-benzylsuccinamide-(SMe)cysteine-nor-cyclostatine is soluble in aqueous media, thus making oral administration feasible. This renin inhibitor, 4-[4-(N-methylamino)piperidine]-(R)-2-benzylsuccinamide-(SMe)cysteine-nor-cyclostatine, is also useful against congestive heart failure and for the treatment of glaucoma.

The activity of 4-[4-(N-methylamino)piperidine]-(R)-2-benzylsuccinamide-(SMe)cysteine-nor-cyclostatine as an inhibitor of the angiotensinogen cleaving activity of renin may be determined by studying its ability to inhibit the angiotensinogen-cleaving activity of renin in vitro.

The renin inhibitor 4-[4-(N-methylamino)piperidine]-(R)-2-benzylsuccinamide-(SMe)cysteine-nor-cyclostatine may be administered for the treatment of glaucoma by direct topical application of a solution to the corneal surfaces.

The renin inhibitor 4-[4-(N-methylamino)piperidine]-(R)-2-benzylsuccinamide-(SMe)cysteine-nor-cyclostatine can also be administered as an antihypertensive agent or agent for the treatment of congestive heart failure by either the oral or parental routes of administration, with the former being preferred for reasons of patient convenience and comfort. In general, these compounds are normally administered orally in dosages ranging from about 0.1 mg to about 20 mg per kg of body weight per day, preferably about 0.1 to about 15 mg per kg of body weight per day, and about 0.1 mg to about 5 mg per kg of body weight per day, preferably about 0.05 to about 1 mg per kg of body weight per day, when given parenterally; variations will necessarily occur depending upon the condition of the subject being treated and the particular compound being administered.

The renin inhibitor 4-[4-(N-methylamino)piperidine]-(R)-2-benzylsuccinamide-(SMe)cysteine-nor-cyclostatine can be orally administered in a wide variety of different dosage forms, i.e., it may be formulated with various pharmaceutically acceptable inert carrier in the form of tablets, capsules, lozenges, troches, hard candies, powders, sprays, aqueous suspensions, elixirs, syrups and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the active compounds of the present invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch (preferably potato or tapioca starch), alginic acid and certain complex silicates, together with binding agents such as polyvinylpyrrolidone, sucrose, gelatin and acacia. Additionally, lubricating agents such as magnesium stearate, sodium lauryl sulfate and talc and compositions of a similar type may also be employed. Lactose or milk sugar as well as high molecular weight polyethylene glycols may be employed as fillers in soft and hard-filled gelatin capsules. When aqueous suspensions and/or elixirs are desired for oral administration, the essential active ingredient therein may be combined with various sweetening or flavoring agents, coloring matter or dyes and, if so desired, emulsifying agents and/or solvents such as water, ethanol, propylene glycol, glycerin or combinations thereof.

The processes of the present invention are illustrated in the following Examples.

All melting points are uncorrected. Optical rotations were taken on a Perkin Elmer Model 241 polarimeter. Unless otherwise indicated, all NMR's are in DMSO-$d_6$. Only significant and diagnostic absorptions are reported.

EXAMPLE 1

Preparation of E-2-Benzylidenesuccinic acid 4-[4-(N-t-butoxycarbonylmethylamino)piperidine]amide:

To 40 ml of 80:20 isopropanol/water was added 4.0 g (21.25 mmol) of benzylidene succinic anhydride followed by 5.0 g (23.37 mmol) of 4-(N-t-butoxycarbonyl-methylamino)-piperidine. Then 1.125 (10.62 mmol) of sodium carbonate ($Na_2CO_3$) was added and the mixture was allowed to stir at 20° C. for 3.5 hours. The reaction mixture was reduced to one-half volume under reduced pressure and then poured into 2.5% hydrochloric acid (HCl) and extracted with ethyl acetate. The ethyl acetate extracts were washed with water and brine then dried with sodium sulfate and evaporated under reduced pressure to yield a tan solid (8.27 g, 97% crude yield). ($^1H$ NMR $\delta$ 1.43 (9H, s), 2.60 (1 H, m), 2.70 (3H, s), 3.09 (1 H, m), 4.50 (1H, br d, J=13), 7.4 (5H, m), 7.76 (1H, s), 12.6 (1H, s)).

EXAMPLE 2

Preparation of rac-2-Benzylsuccinic acid 4-[4-(N-t-butoxycarbonyl-methylamino)piperidine]amide:

The acid from Example 1 (7.0 g, 17.39 mmol) was dissolved in 200 ml of methanol. To this solution was added 0.5 g of 10% paladium on carbon (Pd/C) and the mixture was hydrogenated (20° C., 50 psi) on a Parr shaker for 20 hours. The reaction mixture was filtered and the solvents were removed under vacuum leaving 6.45 g of a foam. ($^1H$ NMR $\delta$ (1:1 mixture of amide rotamers) 1.37 (9H, 2 s), 2.38 (1H, m), 2.62 (3H, 2 s), 3.9 (2H, m), 4.43 (1H, br d, J=13), 7.2 (5H, m), 12.1 (1H, s))

Alternatively, rac-2-Benzylsuccinic acid 4-[4-(N-t-butoxycarbonylmethylamino)piperidine]amide may be prepared in a one step method by dissolving 4-(N-t-butoxycarbonyl-methylamino)-piperidine (16.0 g, 74.6 mmol) in 100 ml of isopropanol and 30 ml of water. Then 4.77 g of sodium carbonate ($Na_2CO_3$) was added followed by 12.8 g (68.0 mmol) of benzylidene succinic anhydride. The mixture was stirred at 20° C. for 6.5 hours then filtered to remove any undissolved solids. Then 1.7 g of 10% Pd/C was added and the mixture was hydrogenated (50 psi, 20° C.) for 4 hours. After filtration, the mixture was reduced to one-half volume by evaporation of solvent under reduced pressure. The residue was diluted with water, acidified to pH 3.0 by addition of 5% hydrochloric acid (HCl) and extracted with ethyl acetate. The ethyl acetate extracts were washed with water and brine and dried with sodium sulfate ($Na_2SO_4$). Evaporation of the solvent left a thick oil which was crystallized from 130 ml of isopropyl ether yielding 19.07 g of a white solid. (m.p.: 118°–120° C. The $^1H$ NMR was identical to that of the material prepared above.)

EXAMPLE 3

Preparation of (S)-(+)-1-Cyclohexylethylamine salt of rac-2-Benzylsuccinic acid 4-[4-(N-t-butoxycarbonyl-methylamino)piperidine]amide:

To 146 ml of a hot acetone solution of 22.63 g (55.3 mmol) of the acid from Example 2 above was added a solution of 7.04 g (55.3 mmol) of (S)-(+)-1-cyclohexylethylamine in 10 ml of acetone. The mixture was allowed to cool to 20° C. After 70 minutes the precipitate was collected by filtration and dried yielding 13.84 g of a white solid ($[\alpha]^{20}_{365} = -6.44$ (c=0.33 methanol)). This material was recrystallized from 260 ml of acetone yielding 9.26 g of a white solid, ($[\alpha]^{20}_{365} = -6.98$ (c=0.32, methanol). One more recrystallization from 260 ml of acetone yielded 4.53 g of a white solid, ($[\alpha]^{20}_{365} = -8.00$ (c=0.33, methanol)). Further recrystallizations did not change the rotation. Two more crops could be obtained by reducing the volume of the mother liquor and collecting the solids. A total of 9.51 g was obtained. ($^1H$ NMR $\delta$ 0.99 (3H, d, J=8), 1.36 (9H, s), 2.10 (1 H, dd, J=6, 16), 2.60 (3H, s), 2.89 (2H, dd, J=6,10), 4.42 (1H, br d, J=14), 7.2 (5H, m)).

EXAMPLE 4

Preparation of (R)-2-Benzylsuccinic acid 4-[4-(N-t-butoxycarbonylmethylamino)piperidine]amide:

The salt from Example 3 above (9.51 g, mmol) was slurried in water and 5% hydrochloric acid was added until a stable pH of 3.0 was obtained. The mixture was extracted with methylene chloride and the methylene chloride extracts were washed with water and dried with sodium sulfate ($Na_2SO_4$). Removal of the solvents under vacuum left 7.3 g of a white solid which was recrystallized from 45 ml of isopropyl ether yielding 6.77 g of a white solid (30.3% weight yield from Example 2, 60.6% of the desired enantiomer) (m.p. 135°–137° C. $[\alpha]^{20}_{365} = +7.77°$ (c=0.39, methanol). $[\alpha]^{20}_D = +1.62°$ (c=0.39, methanol). The $^1H$ NMR was identical to the racemic material prepared above.)

EXAMPLE 5

Preparation of 4-[4-(N-t-butoxycarbonyl-methylamino)piperidine]-(R)-2-benzylsuccinamide-(SMe)cysteine-nor-cyclostatine:

t-Butoxycarbonyl-(SMe)cysteine-nor-cyclostatine (438 mg, 0.95 mmol) was dissolved in 15 ml of methylene chloride and cooled in an ice bath. Methanesulfonic acid (274 mg, 2.86 mmol) was added as a solution in 5 ml of methylene chloride. The reaction mixture was allowed to warm to room temperature and stirred for 7 hours. The solution was washed with 0.5M sodium hydroxide and water and then dried with sodium sulfate ($Na_2SO_4$). After filtration, the acid from Example 4 above (351 mg, 0.87 mmol) was added followed by 2-ethoxy-1-ethoxycarbonyl-1-2-dihydroquinoline, (259 mg, 1.05 mmol). The reaction was stirred at 20° C. for 18 hours then washed with 5% HCl, water and brine. After drying over sodium sulfate ($Na_2SO_4$), the solvents were removed under reduced pressure leaving 468 mg of the title compound as a viscous oil (72% crude yield). ($^1H$ NMR δ(~1:1 mixture of amide rotamers) 2.08 (3H, s), 2.62 (3H, 2 NMe), 3.88 (1H, m), 3.99 (1H, dd, J=3,7), 4.20 (1H, m), 4.28–4.50 (2H, m), 4.85 (1H, septet, J=7), 5.31 (1H, d, J=7), 7.2 (5H, m), 7.55 (1H, 2, J=8), 8.22 (1H, d, J=8))

EXAMPLE 6

Preparation of 4-[4-(N-t-butoxycarbonyl-methylamino)piperidine]-(R)-2-benzylsuccinamide-(SMe)cysteine-OMe:

HCl-(SMe)cysteine-OMe (963 mg, 5.19 mmol) was slurried in 55 ml of methylene chloride (cooled in an ice bath). To this was added triethylamine (525 mg, 5.19 mmol) and the mixture was stirred for 25 minutes at 0° C. Then the product from Example 5 above (2.0 g, 4.9 mmol) was added followed by 2-ethoxy-1-ethoxycarbonyl-1-2dihydroquinoline (1.283 g, 5.19 mmol). The ice bath was removed and the mixture was allowed to warm to room temperature and stir for 18 hours. After dilution with methylene chloride the mixture was washed with 5% HCl, saturated aqueous sodium bicarbonate ($NaHCO_3$) and brine and then dried with sodium sulfate ($Na_2SO_4$). Filtration and removal of the solvents gave 2.68 g (100% crude yield) of a foam. ($^1H$ NMR (approximately 1:1 mixture of amide rotamers) δ 1.38 (9H, 2), 2.06 (3H, s), 2.11 (1H, m), 2.60 (3H, 2), 3.59 (3H, s), 3.90 (2H, m), 4.42 (2H, m), 7.2 (5H, m), 8.45 (1H, d, J=8))

EXAMPLE 7

Preparation of 4-[4-(N-t-butoxycarbonyl-methylamino)piperidine]-(R)-2-benzylsuccinamide-(SMe)Cysteine-OH:

The ester from Example 6 (2.65 g, 4.94 mmol) was dissolved in a mixture of 30 ml of acetonitrile and 30 ml of phosphate buffer (0.25M pH 7.5). Then 150 mg of papain (Solvay) was added along with 75 mg of L-cysteine (to activate the papain). After stirring for 40 minutes thin layer chromatography (100% ethyl acetate) indicated that the hydrolysis was complete. The acetonitrile was removed by evaporation under reduced pressure and dilute aqueous sodium bicarbonate ($NaHCO_3$) was added to bring the pH of the solution to approximately 10. After washing the ethyl acetate, the aqueous layer was slowly acidified to pH 3 and extracted with ethyl acetate. The ethyl acetate extracts were washed with brine and dried with sodium sulfate ($Na_2SO_4$). Removal of the solvents left 1.92 g of a white foam. ($^1H$ NMR (~1:1 mixture of amide rotamers) δ 1.39 (9H, 2), 2.09 (3H, 2), 2.11 (1H, m), 2.61 (3H, 2), 3.90 (2H, m), 4.40 (2H, m), 7.2 (5H, m), 8.29 (1H, d, J=8), 12.7 (1H, br s))

EXAMPLE 8

Preparation of 4-[4-(N-t-butoxycarbonyl-methylamino)piperidine]-(R)-2-benzylsuccinamide-(SMe)cysteine-nor-cyclostatine:

The acid from Example 7 (1.90 g, 3.64 mmol) was dissolved in 90 ml of methylene chloride then nor-cyclostatine (1.06 g, 4.37 mmol) and 2-ethoxy-1-ethoxycarbonyl-1-2-dihydroquinoline (1.08 g, 4.37 mmol) were added. The mixture was stirred at 20° C. for 18 hours then diluted with methylene chloride and washed with 5% HCl, saturated aqueous sodium bicarbonate ($NaHCO_3$) and brine. After drying with sodium sulfate ($Na_2SO_4$) and filtration the solvents were removed under reduced pressure yielding 2.62 g of a white foam. The $^1H$ NMR was identical to the material prepared above.

EXAMPLE 9

Preparation of 4-[4-(N-methylamino)piperidine]-(R)-2-benzylsuccinamide-(SMe)cysteine-nor-cyclo-statine Hydrochloride:

Gaseous hydrogen chloride was bubbled through 7 ml of acetonitrile for approximately 5 seconds. This solution was cooled to 0° C. and 200 mg of the product from Example 8 was added. The cooling bath was removed and the reaction mixture allowed to warm to room temperature. After 40 minutes thin layer chromatography (100% ethyl acetate) indicated that the deprotection was complete. The solvent was evaporated under vacuum and the residue was dissolved in 10 ml of ethyl acetate and diluted with 0.2 ml of water. Then 10 ml of the ethyl acetate/water azeotrope was distilled out and replaced with dry ethyl acetate to keep a constant volume in the distilling flask. The distillation flask was seeded with 4-[4-(N-methylamino)piperidine]-(R)-2-benzylsuccinamide-(SMe)cysteine-nor-cyclostatine hydrochloric salt and the mixture stirred overnight at 20° C. The white solid that had precipitated was collected by filtration and after vacuum drying yielded 104 mg (57%) of the title compound. ($^1$H NMR δ (1:1 mixture of rotamers) 2.08 (3H, 2), 2.49 (3H, 2), 3.89 (1 H, m), 3.99 (1H, m), 4.19 (1 H, m), 4.32 (2H, m), 4.82 (1H, septet, J=7), 5.32 (1 H, m), 7.2 (5H, m), 7.55 (1H, d, J=8), 8.22 (1H, m), 9.06 (2H, br s)).

I claim:

1. A process for preparing the diastereomeric salt known as (R)-2-benzyl-succinic acid 4-[4-(N-t-butoxycarbonyl-methylamino)-piperidine]amide S-(+)-1-cyclohexylethylamine substantially free of the (S)-enantiomer, which comprises reacting S-(+)-1-cyclohexylethylamine with either racemic or an optionally active mixture of 2-benzylsuccinic acid 4-[4-(N-t-butoxycarbonyl-methylamino)-piperidine]amide.

2. A process according to claim 1, wherein the diastereomeric salt known as (R)-2-benzylsuccinic acid 4-[4-(N-t-butoxycarbonyl-methylamino)piperidine]amide S-(')-1-cyclohexylethylamine is neutralized to form (R)-2-benzylsuccinic acid 4-[4-(N-t-butoxycrabonylmethylamino)piperidine]amide.

3. A process according to claim 1 which is carried out in a solvent selected from acetone, acetonitrile, ethyl acetate, methyl ethyl ketone and 2-propanol.

4. A process according to claim 3 which is carried out in an acetone solvent.

5. A process according to claim 2 which is carried out in a solvent selected from acetone, acetonitrile, ethyl acetate, methyl ethyl ketone and 2-propanol.

6. A process according to claim 5 which is carried out in an acetone solvent.

7. A process for preparing the diastereomeric salt known as S-2-benzylsuccinic acid 4-[4-(N-t-butoxycarbonyl-methylamino)-piperidine]amide (R)-(−)-1-cyclohexylethylamine substantially free of the (R)-enantiomer, which comprises reacting (R)-(−)-1-cyclohexylethylamine with either racemic or an optically active mixture of 2-benzylsuccinic acid 4-[4-(N-t-butoxycarbonyl-methylamino)piperidine]amide.

8. A process according to claim 7, wherein the diastereomeric salt known as (S)-2-benzylsuccinic acid 4-[4-(N-t-butoxycarbonyl-methylamino)piperidine]amide (R)-(−)-1-cyclohexylethylamine is neutralized to form (S)-2-benzylsuccinic acid 4-[4-(N-t-butoxycarbonyl-methylamino)-piperidine]amide.

9. A process according to claim 7 which is carried out in a solvent selected from acetone, acetonitrile, ethyl acetate, methyl ethyl ketone and 2-propanol.

10. A process according to claim 9 which is carried out in an acetone solvent.

11. A process according to claim 8 which is carried out in a solvent selected from acetone, acetonitrile, ethyl acetate, methyl ethyl ketone and 2-propanol.

12. A process according to claim 11 which is carried out in an acetone solvent.

* * * * *